United States Patent [19]

Bisconte

[11] Patent Number: 5,306,420
[45] Date of Patent: Apr. 26, 1994

[54] MODULAR DEVICE FOR COLLECTING, INCUBATING, AND FILTERING MULTIPLE SAMPLES

[75] Inventor: Jean-Claude Bisconte, Briis-Sous-Forges, France

[73] Assignee: Biocom Societe Anonyme, Les Ulis, France

[21] Appl. No.: 910,162

[22] PCT Filed: Jan. 25, 1991

[86] PCT No.: PCT/FR91/00044
§ 371 Date: Jul. 14, 1992
§ 102(e) Date: Jul. 14, 1992

[87] PCT Pub. No.: WO91/11245
PCT Pub. Date: Aug. 8, 1991

[30] Foreign Application Priority Data
Jan. 26, 1990 [FR] France .................. 90 00959

[51] Int. Cl.$^5$ ............................ B01D 35/30
[52] U.S. Cl. ........................ 210/143; 55/490;
73/863.23; 210/232; 210/541; 422/101;
422/104; 435/311
[58] Field of Search ............ 422/104, 103, 101, 63,
422/67; 435/311; 210/232, 143, 416.1, 445, 450,
455, 498, 340, 407, 335, 541; 55/270, 271, 272,
490; 73/863.23, 863.24, 864.34

[56] References Cited

U.S. PATENT DOCUMENTS

| | | | |
|---|---|---|---|
| 3,540,858 | 11/1970 | Rochte et al. | 422/101 |
| 3,730,352 | 5/1973 | Cohen et al. | 210/332 |
| 4,427,415 | 1/1984 | Cleveland | 422/101 |
| 4,493,815 | 1/1985 | Fernwood et al. | 422/101 |
| 4,834,946 | 5/1989 | Levin | 422/101 |
| 4,948,442 | 8/1990 | Manns | 422/101 |
| 5,108,704 | 4/1992 | Bowers et al. | 422/101 |
| 5,190,666 | 3/1993 | Bisconte | 210/143 |

FOREIGN PATENT DOCUMENTS

| | | | |
|---|---|---|---|
| 8203690 | 10/1982 | European Pat. Off. | 422/101 |
| 2638101 | 4/1990 | France . | |
| 2638240 | 4/1990 | France | 210/232 |
| 558669 | 2/1975 | Switzerland | 210/445 |
| 2176601 | 12/1986 | United Kingdom . | |

*Primary Examiner*—Joseph W. Drodge
*Attorney, Agent, or Firm*—Bell, Seltzer, Park & Gibson

[57] ABSTRACT

A filter device for a plurality of liquid or gaseous fluid samples containing particles to be filtered, the device comprising a stand, at least one filter, upstream and downstream clamping blocks cooperating wit the filter and designed to be fixed together with an interposed perforated sealing gasket and are configured to be inserted through an opening in the stand, forced filtering mechanism and filtrate evacuation mechanism. The upstream clamping block is a removable independent tank block for enabling pretreating of samples introduced in wells thereof.

16 Claims, 1 Drawing Sheet

MODULAR DEVICE FOR COLLECTING, INCUBATING, AND FILTERING MULTIPLE SAMPLES

BACKGROUND OF THE INVENTION

The present invention relates to a modular device for collecting, incubating, and filtering multiple samples.

The use of filter membranes is becoming increasingly fashionable in applications relating to analyzing particles, cells, and bacteria. The calibrated membranes made of polycarbonate produced by firms such as Nucleopore and Millipore have remarkable properties as to their qualities of recovering particles of determined sizes.

They are very fine, they withstand chemical agents, and they lend themselves well to observation under the microscope, either with reflected light or with transmitted light. With transmitted light, it is necessary for the membrane to be transparent in order to make observation possible. With epifluorescent illumination, and providing the cells and bacteria have been stained with a fluorochrome such as acridine orange, observation shows pale particles on a dark background.

In 1980, Pettipher proposed this method for direct observation of raw milk bacteria for the purposes of quality control. The complex composition of milk and the presence of a high number of cells (several tens of thousands) makes it impossible to filter the samples without prior treatment. The pretreatment consists in treating the milk with a mixture of detergent and trypsin. Under specific conditions of concentration and of timing, the caseine micelles and the fat globules are decomposed and the cells are digested without significantly changing the germ content, thus enabling the germs to be stained.

Filtering is performed on filters of large dimensions using suction. After applying various washes, the stain is applied followed by further washes. This method known as the Direct Epifluorescence Technique (DEFT) presents numerous advantageous. The filtering gives rise to a considerable concentration of events to be counted.

Compared with indirect methods which require information about bacteria to be amplified by proliferation (2 to 3 days), direct methods are supposed to give a quick result. Concentration by filtering can give excellent sensitivity providing the carrier medium is highly filterable The main handicap is the complexity of the method and the sensitivity of its results to preparation and measurement conditions.

Observation is performed under the microscope and when event densities are low, fluctuations in distribution over the filter make it necessary to perform counting in numerous microscope fields. For example, in the application of monitoring raw milk for densities of about 50,000 FCU/ml (FCU =Formant Colony Unit), the DEFT method gives rise to distributions of the order of less than one bacterium per microscope field. In addition, the very poor mechanical properties of the polycarbonate membrane and its fineness make observation under the microscope very difficult.

Placed between slide and cover slip, the combined deformations of the glass slide, of the membrane, and of the microscope stage explain why attempts at performing analysis automatically have been unsuccessful. In spite of the existence of automatic focusing devices, losses of focus are inevitable and a major portion of analysis time is spent in finding focus.

In 1988, Bisconte proposed two solutions which largely satisfy the problems raised and which constitute the subject matter of two patent applications. U.S. Pat. No. 5,190,666, relates to a device making it possible to process several tens of samples automatically and in parallel on the same filter. A second patent application, FR-88 13805, relates to the combination of a means for restraining filters and for placing them on a microscope stage by making use of suction.

The first solution, which integrates the presence of filters mounted in this way in support frames, provides a solution to the question of passing a plurality of samples to be filtered simultaneously, independently, and in parallel, by making use simultaneously of pressure and of suction. In that solution, a receptacle having multiple wells is put into communication with the filter by capillary tubes. The capillaries enable samples and reagents to pass through in succession.

The main drawback of that disposition is to make it difficult to wash the ducting (risk of contamination and stain residues).

The second solution consists mainly in mounting the filters in a semi-rigid support with position indexing. The filter is placed initially in the filtering system in an exact position by means of centering studs. Studs present on the microscope guarantee corresponding positioning during observation. In this way, multiple deposits present on the filter, even if very small in size, can easily be found by a computer program applying X and Y drive to the microscope stage.

The present invention seeks to improve the device for filtering and preparation and to make it simpler and modular, while retaining the same basic concept.

SUMMARY OF THE INVENTION

The present invention provides a filter device for filtering a plurality of liquid or gaseous fluid samples containing particles to be filtered such as bacteria, cells, or other elements, in particular as contained in milk or blood, the device comprising:

i) a stand;

ii) at least one filter;

iii) means enabling parallel filtering to be performed on the same filter, i.e. simultaneous and independent filtering of said fluid samples, and comprising:

a) at least one gasket including a plurality of perforations passing through its thickness, said filter being applied against a face of said perforated gasket;

b) clamping means for the perforated gasket and thus for the filter, which clamping means are constituted by a first perforated block disposed upstream and a second perforated block disposed downstream in the filtering direction, and enabling a plurality of independent and mutually sealed filter zones to be delimited on said filter corresponding to the perforations through the gasket and through the upstream and downstream blocks;

c) forced filtering means for filtering each of said fluid samples through said independent filter zones;

iv) filtrate evacuation means; which filter device is characterized in that the upstream perforated clamping block is made in the form of a tank, the perforations through said block defining a corresponding number of wells for storing the samples to be filtered and for conveying substances for treating the particles retained after filtering in each of the independent filter zones for microscopic analysis of said particles outside the filter device.

In a preferred embodiment of the device of the invention, in the event that the samples need to be pretreated prior to filtering:

the tank-block is removable and designed to receive the samples outside the filter device, removable closure means for its well-forming perforations being provided for this purpose at least on its upstream face;

the downstream perforated clamping block is made in the form of a removable tray for pressing against the downstream face of the tank-block with the filter and the perforated gasket being interposed therebetween and after the samples have been pretreated, and to be inserted into the stand after the assembly constituting the tank-block and the tray has been turned over and after the closure means have been removed from the upstream face of the tank-block, said tray being inserted like a drawer together with the tank-block which it supports for the purpose of filtering the samples therein that have been pretreated in this way, the upstream face of the filter drawer and the downstream face of the tank-block together with the perforated gasket and the filter which are interposed therebetween being provided with complementary indexing means ensuring that the perforations of the gasket are in alignment with the perforations of the tank-block and of the filter drawer, additional fixing means being provided on the side faces of the tank-block and on the filter drawer to ensure that the two blocks are clamped together in sealed manner.

In an advantageous disposition of this preferred embodiment, the stand has:

a front opening enabling the tank-block and the filter drawer to be inserted therein, and also enabling the evacuation means to be inserted therein;

two horizontal slideways formed on the vertical sides of the stand delimiting the front opening and being designed to enable the filter block and the tank-block it supports to be inserted therein;

a bottom opening through the bottom face of the enclosure and in communication with the perforated face of the evacuation means;

a top opening formed through the top face of the enclosure to enable forced filtering means to be applied to the tankblock, with an interposed sealing gasket; the filter drawer including snap-fastening clips for engaging studs projecting from the side faces of the tank-block for the purpose of holding these two blocks clamped against each other in sealed manner, and being applied in sealed manner with an interposed sealing gasket against the evacuation means when the drawer is inserted in the slideways.

In an advantageous mode of this disposition, the forced filtering means are means for applying pressure to the samples contained in the wells of the tank-block and are provided in a moving head including a pressurizing chamber whose floor has a first plurality of tubes passing therethrough, which tubes are calibrated and designed to be inserted in part into the ducts of the upstream tank-block and communicating with an inlet for air under pressure provided through the ceiling of said chamber, the outside diameter of the calibrated tubes being substantially equal to the inside diameter of the wells, said chamber being movable under drive from actuator means such as an actuator.

In another advantageous disposition, the closure means for at least the upstream face of the tank-block is constituted by a plate including a plurality of plugs for inserting into corresponding wells of the tank-block.

In a preferred variant of this disposition, the closure means for at least the upstream face of the tank-block is constituted by a discardable adhesive membrane and the calibrated tubes of the forced filtering means are chamfered, enabling said membrane to be left in place and then punctured locally by the chamfered tubes when the said forced filtering means are applied.

In yet another advantageous disposition, the ceiling of the pressurizing chamber has a plurality of tubes passing therethrough and received inside the calibrated tubes in the floor of said chamber, the ceiling tube being in communication with a device for feeding a substance for treating the particles retained by the independent filter zones after the samples have been filtered, which substance is constituted, in particular, by a stain reagent, a washing liquid, hot air for drying, or any other substance.

In accordance with the invention, in the event that double filtering is necessary for the samples, the device includes two filters having different pore sizes placed on opposite sides of the perforated gasket, the filter having the smaller-diameter pores being placed downstream.

Alternatively, the evacuation means is removable and is constituted by a block which is identical to the tank-block and which includes removable closure means for its downstream face, said evacuation means constituting a tank being intended, after the first filtering operation, to replace the upstream tank-block and to be replaced by normal evacuation means so as to enable the second filtering operation to be performed on a second filter that replaces the first filter carried by the filter drawer.

In a preferred variant applicable to double filtering, the device of the invention includes a second tank-block and a second filter drawer with a second perforated gasket and a second filter being interposed therebetween, and being disposed in cascade relative to the first tank-block and to the first filter drawer, the stand including two further horizontal slideways for enabling the second filter drawer to be inserted therein together with the second tank-block it supports.

In accordance with the invention, the forced filtering means further include filtrate suction means in communication with the evacuation means, and co-operating with the forced filtering means that apply pressure.

Advantageously, the filter drawer is designed to co-operate with a plurality of mutually identical tank-blocks with the number of blocks being a function of the number of samples.

Also in accordance with the invention, the filter device includes a computer for controlling the forced filtering and the treatments of the particles retained by the independent filter zones after filtering.

In addition to the above dispositions, the invention further includes other dispositions, which appear from the follow description.

BRIEF DESCRIPTION OF THE DRAWINGS

The invention will be better understood from the following additional description which refers to the accompanying drawing, in which.

Figure 1:
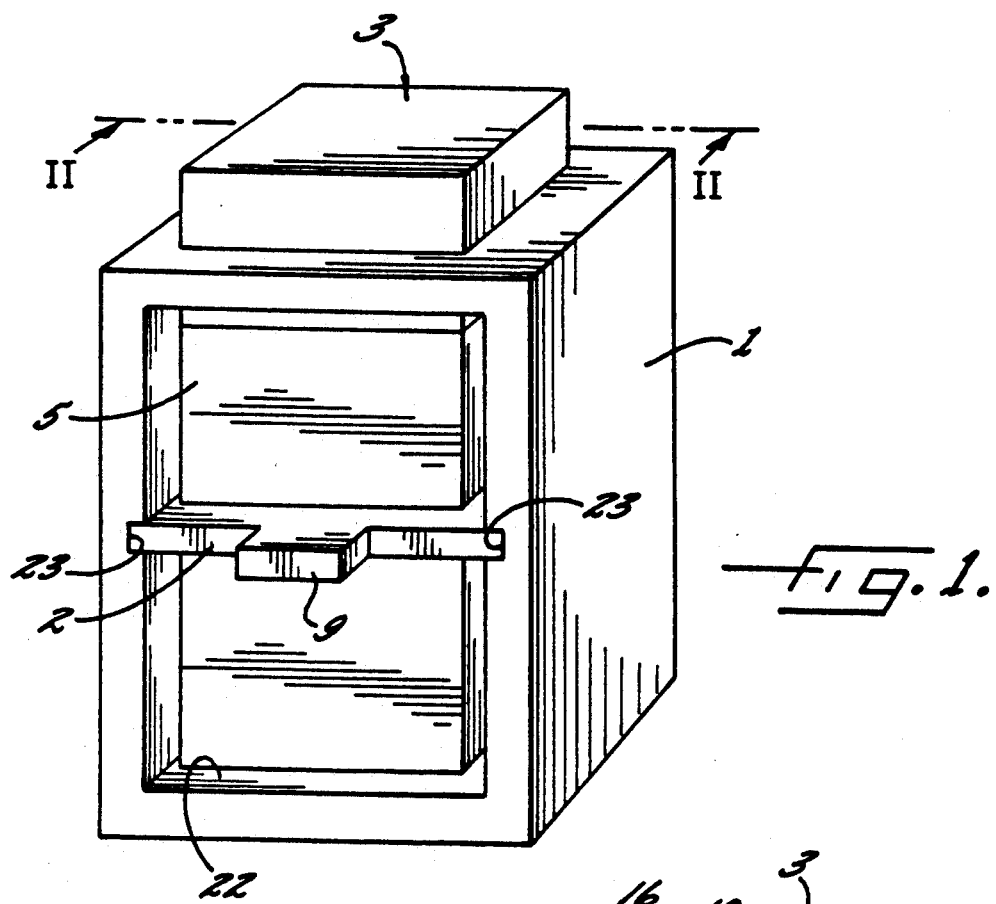
FIG. 1 is a diagrammatic perspective view of the filter device of the invention.

It must nevertheless be understood that the drawing and the corresponding portions of the description are given purely to illustrate the subject matter of the invention and that they do not constitute any kind of limitation thereon.

DETAILED DESCRIPTION

The originality of the solution proposed in the present invention consists essentially in that it makes it possible to combine in a single element the function of treating the samples (e.g. collecting, incubating, digesting, etc. . . . ) prior to filtering while outside the filter device, and the function of treating the particles of each sample as retained by the filter (e.g. washing, staining, drying, etc. . . . ) after filtering and while they are inside the filter device itself. this is done with a tank-block.

The concept of the removable tank-block has the following advantages:

a plurality of blocks of this type can be used having wells (or ducts) that are open at both ends. The blocks are thus simple, easy to clean, and can be very numerous so that the filtering device can handle a large the number of samples; and after filtering, the wells are used for directing the flow of reagents towards the filter; the circuits containing the samples are thus completely dissociated from the reagent circuits, thereby eliminating risks of contamination.

Similarly, the sealing ring is removable and is easily replaced.

The principle is as follows: rectangular blocks (or blocks of any other shape) are pierced by 24 parallel (or converging) cylindrical holes that are open at both ends. A closure plate having 24 flexible plugs (rubber type plugs) is placed on one of the faces. Discardable adhesive membranes could also be used. The 24 sample wells can thus be filled using an automatic dispenser (not shown), e.g. of the type sold under the trademarks Tecan(®) or Gilson(®), or by a manual system of the standard multipipette type (in which case a well spacing of 9 mm is a conventional arrangement).

The dispenser can be used for filling tens of tank-blocks which can then be treated by automatic machines. Depending on the time between filling and filtering, a closure plate may be placed not only over the bottom face, but also over the top face to avoid evaporation and contamination.

The other important point is that the filter is placed in a second perforated block that acts as a filter drawer, which is itself removable. This drawer, previously fitted with a filter and a sealing gasket, is placed in sealed manner against the top face of the tank-block while outside the filter device, but after removing the corresponding closure plate, if any. At this stage, the block is thus closed over both faces, firstly by the bottom closure plate and secondly by the drawer carrying the filter against its top face. The block can then be turned upsidedown and inserted into the filter device.

In a very simple configuration, it suffices merely to apply suction beneath the filter drawer and to remove the bottom closure plate which is now on top after the tank-block has been turned upsidedown. The description below relates more particularly to a filter device that is more complex, making it possible to apply pressure automatically upstream of the filter and, where appropriate, suction downstream therefrom, and which includes a dispenser (not shown and preferably automatic, of known type for the person skilled in the art) serving to feed reagents into the tank-block after the samples have been filtered.

There follows a brief general description of the filter device, which comprises the following main elements a stand (or enclosure) 1: it is intended to support the various components rigidly;

a filter drawer 2: it is intended to support the filter(s) and the tank-blocks one after another;

a moving head 3: it is actuated by an actuator 4 and serves to inject reagents and gaseous fluids while enabling forced filtering to be performed by putting the samples under pressure:

a multiple function tank-block 5: this block initially contains the samples to be filtered, and subsequently contains the reagents;

an emptying device 6: it collects the filtrates and enables them to be evacuated;

an extractable perforated gasket 7: it is placed between the tank-block and the filter drawer, itself carrying the filter 13; and a filter 13: the filter is clamped between the drawer 2 and the perforated gasket 7.

The above general description is followed by a detailed description of the various components.

The stand 1: is machined in light alloy, the stand being in the form as a rectangular volume that is open to the front (cf. opening 22 in FIG. 1). It carries the moving head 3 at its top, which head has access to the inside of the device via an opening 24, and it has two horizontal slideways or grooves 23 which are provided in the vertical side walls of the stand 1 and in which the filter drawer 2 slides. At the bottom there is an orifice 8 enabling suction to be applied to the filtrates by means of a suction device (not shown) communicating with the emptying device 6.

The filter drawer 2: is machined in stainless steel or any other rigid material that withstands chemical corrosion. This drawer includes a handle 9 in its front face for facilitating invention and extraction of the drawer.

The drawer carries two stainless clips 10 serving to secure the tank-block firmly in place. The drawer is pierced by 24 calibrated holes 11. The perforations through the drawer are closed on top by a grid 12 and on which the filter 13 bears. The drawer carries studs (not shown) which pass through the filter and the gasket and which engage in the tank-block 5, thereby ensuring that these components are in alignment.

The moving head 3 itself comprises a stationary portion 25 fixed to the stand 1 and a moving portion proper 14 capable of moving upwards under drive from an actuator 15. The moving head includes a space 16 into which 24 feed tubes 18 emerge for the purpose of injecting reagents into the 24 wells of the block 5 after they have been connected to an automatic dispenser device (not shown). A compressed air feed 19 enables a chamber 17 to be put under pressure. This chamber includes 24 chamfered tubes 20 fixed to its floor 29 having the feed tubes 18 passing along the bores thereof and fixed to the ceiling 29a of said chamber. The moving head includes a gasket 21 for establishing sealing with the block 5.

The tank-block 5 is in the form of a rectangular parallelepiped made of metal or of synthetic material (depending on requirements). It is pierced by 24 holes or ducts 30 that are open at both ends. The portions of these holes facing the filter are tapering and calibrated. Studs 26 disposed on the sides of the block are engaged by the clips 10 of the filter drawer 2.

The tank-block includes openings (not shown) for alignment and keying purposes enabling all of the elements such as the filter and the gasket, together with the filter drawer to be located as mentioned above.

The emptying device 6 is a tank made of light material. It preferably has the same outside dimensions as a tank-block. It is provided with top and bottom sealing gaskets 27 and 28.

The perforated and extractable gasket 7 is a plate of crushable flexible material pierced by 24 holes. Two holes (not shown) have the studs of the filter drawer passing therethrough thus ensuring that the 24 orifices of the block 5 and the 24 orifices of the filter drawer 2 are in alignment, as described above.

The filter 13 is of the type used in the context of U.S. Pat. No. 5,190,666. It comprises a filter membrane tensioned in a semi-rigid frame made of plastic. Openings (not shown) enable the above-mentioned alignment studs of the filter drawer to pass through.

Figure 2:
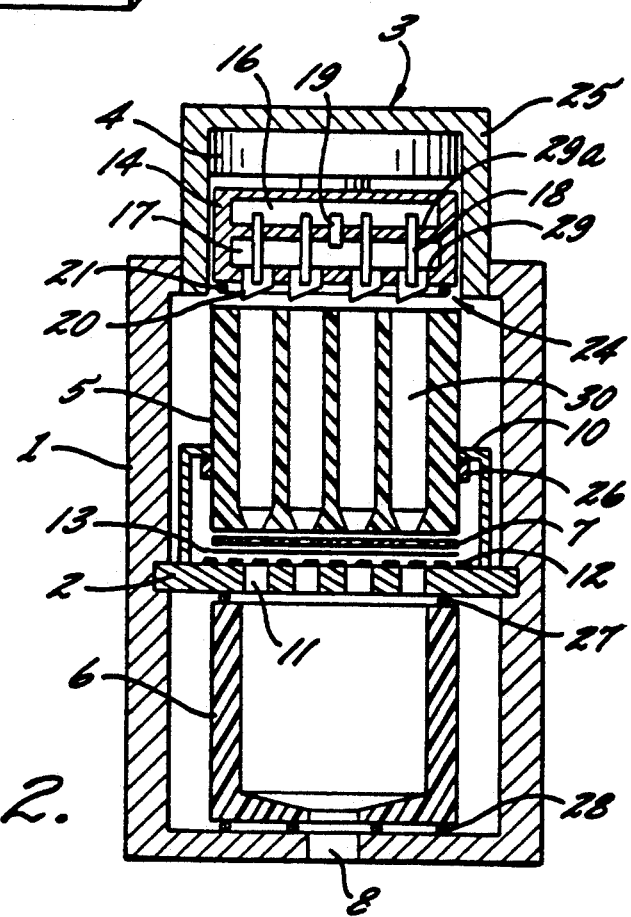
FIG. 2 is an equally diagrammatic section view on II through the device shown in FIG. 1.

With respect to the diagrammatic illustration of the filter device in FIG. 2, it should be observed that the tank-block 5, the perforated gasket 7, and the filter 13 are shown as being separate from the filter drawer 2 in order to make the drawing more intelligible, but it is clear that all of these elements are clamped together in mutual contact.

The operation of the filter device is described below under headings 1 to 4.

1. Utilization of the tank-block: the tank-block 5 is intended to receive in succession the samples to be filtered, the washing reagents, the stains, and gases such as air for expelling the liquid or for drying the filter(s). It can be used before or after being fixed to the drawer. It may also be used as an incubation receptacle.

* Utilization prior to being fixed on the drawer: the tank-block 5 may be provided with closure plates (not shown) on its top and bottom faces. One end can thus be closed, and the samples can be placed in the wells 30 for storage or incubation. A top closure plate prevents evaporation or contamination. To proceed with the filtering and staining stages, the tank-block is turned upsidedown (top face at the bottom). The top closure plate is removed while the bottom plate is kept on the other face.

After initially being fitted with the filter 13 and then the perforated gasket 7, the filter drawer 2 is turned upsidedown and pressed against the block 5. Firm pressure crushes the perforated gasket 7 and the clips 10 snap onto the studs 26 of the block 5. The drawer carrying the assembly fixed together rigidly in this way is turned over, the closure plate is removed, and the drawer can be inserted in the slideways 3 of the stand 1.

* Direct utilization: the filter drawer is disengaged by 1 from the stand, the filter and the gasket are installed as above, and then the tank block is snapped into place in its normal position, with all of the closure plates being removed.

Samples can then be inserted, with the filter preventing the samples escaping prematurely before pressure and/or suction is applied (this is true only for filters having pores of small dimensions). The drawer is then pushed into place and the process can begin. It is also possible to push in the drawer before filling the wells. The filling procedure then takes place via the filling tubes 18, automatically or manually, so long as there is no reason to fear contamination.

The multiple function tank-block can receive various liquid or gaseous mediums. This may be particularly useful in a bio-technology application.

* Biotechnological utilization: the sterilized tank-block receives a filter and is placed on the drawer as before. A suspension of cells is put into its wells. When placed in an incubator, the cells can proliferate because of the nutritient medium of the suspension. The filter then tends to become covered with a mat of cells. The different inlets for each of the wells makes it possible to insert substances to be tested, automatically or manually. Conversely, beneath the filter, samples can be taken regularly to identify the substances produced by the cells. At the end of a variable culture time, the drawer can be removed, the tank-block can be turned over, the liquids can be evacuated, and the filter removed. It is thus possible to obtain living cells or to run a complete culture process terminating with fixing, staining, and automatic observation of the results. This constitutes means for testing molecules very rapidly and simply for their effects on cell proliferation and differentiation.

2. Utilization of the filter drawer: this drawer which is independent of the stand, i.e. is removable, enables the filter, the gasket, and the tank-blocks to be fixed together. When inserted in the slideways of the stand and pushed home, the drawer automatically positions the tank-block in correspondence with the feed orifices for reagents and for pressure. In a variant configuration, the drawer may be provided with couplings to each of the openings: it is thus possible to collect the filtrates individually or to track each filter operation. To do this, it suffices merely to terminate each of the flexible tubes in a collecting test tube. In another, preferred variant, all of the collection tubes are placed in a sealed box in which suction can be established.

3. Description of a complete sequence. Application to analyzing the cells and bacteria in raw milk (DEFT method): an automatic dispenser injects a determined quantity of a sample of raw milk plus a mixture of Triton (a detergent) and trypsin into each of the wells of the tank-block. During this stage, each block is closed at its bottom end by a closure plate (a cover having multiple plugs). The wells are also closed on top and they are placed in incubation. The effect of this treatment is to make the milk more filterable. The volumes treated are about 200 $\mu l$ of milk and the same amount of reagents. The volume of each well is 3 ml. After incubation, each of the blocks is turned over and opened at its filter face. The drawer fitted with the filter and the gasket is snapped into place on a tank-block. Under such circumstances, it should be observed that the filter is a 0.6 $\mu m$ polycarbonate membrane for retaining bacteria. After the drawer has been inserted and the top closure plate has been removed from the tank-block, the sequence begins. It should be observed that the apparatus implemented includes an automated environment capable of automatically pumping liquids and alternating the application of pressure and/or suction with the addition of liquid (this particular method of operation is described, in particular, in patent application FR-88 13804).

Sealing: the actuator 4 (in particular a pneumatic actuator) is actuated. It lowers the moving portion 14 of the head 3 which presses very firmly against the tank-block 5 via a gasket 21. It should be observed that the clearances allow these forces to be transmitted to the block 5 which thus presses against and crushes the perforated gasket 7. This guarantees that the paths remain independent and that there is no untimely mixing of the samples during filtering.

Filtering the milk: a programmed computer for controlling the filter device applies pressure to the wells via the pressure inlet 19, said pressure being applied to the chamber 17 which in turn transmits it to the chamfered tubes 20. All of the wells empty together with differences that are of little significance. It should be observed that suction may be applied in the emptying receptacle 6 in order to increase the gradient. The emptying stage takes 5 to 10 seconds.

Washing and staining: several reagents then follow one another. They are delivered in parallel via the 24 pipes 18. These pipes are in line with the wells and they penetrate about 1 centimeter into them.

The following then follow one another: washing media, pH buffers, and finally acridine orange, a fluorescent stain.

The volumes are about 100 μm per reagent and the sum of the reagents and of the sample is calculated so that even in the event of a filter becoming accidentally clogged, the total volume remains less than the capacity of a well, i.e. 3 ml.

The device is programmed so that the stain remains in contact with the filter and the bacteria deposited thereon for 2 minutes. After final washing and emptying, air is passed through for 2 minutes to dry the filter completely. The drawer 2 can then be removed from the tank-block 5, its clips 10 disengaged, the block 5 removed, and then the filter 13.

The filter is then placed on a special microscope observation stage, such as that described in patent application FR-88 13805.

4. Double filtering: in some cases, it may be advantageous to collect two different types of particles or cells. It is thus possible to place two filters having very different pore sizes on either side of the perforated gasket 7. These filters are thus 2 mm apart and they do not come into contact.

It is also possible to perform double filtering sequentially. Under such circumstances, the receptacle (6) is replaced by a block identical to the block 5 which is closed merely by its filter face. The filtrates are then uniformly distributed in the wells. In another advantageous variant, the second block 5 may also be provided with a filter and with a filter drawer. Under such conditions, pressure is applied to the top block and suction to the bottom block (the device for applying suction is not shown). Naturally, it would be necessary to modify the stand in order to form two other slideways for the second filter drawer.

As can be seen from the above, the invention is not limited in any way to those implementations, embodiments, and applications that are described in detail above. On the contrary, the invention extends to any variants that may occur to the person skilled in the art without going beyond the ambit or the scope of the present invention. In particular, it should naturally be understood that although not essential, it is advantageous for the device for feeding the substances for treating the particles retained by the independent filter zones to be automatic and programmable, the same applying to the forced filtering means, i.e. the means for applying pressure and/or suction may themselves be programmable, with the entire assembly being under the control of a controlling computer.

I claim:

1. A filter device for a plurality of liquid or gaseous fluid samples containing particles to be filtered, the device comprising:
   a stand;
   at least one filter;
   an assembly comprising upstream and downstream clamping blocks cooperating with said at least one filter ad designed to be fixed together with an interposed perforated sealing gasket, said upstream clamping block comprising a plurality of wells for storing samples to be treated, said downstream clamping block being make int he form of a removable perforated tray, said wells, the perforation of said removable tray and the perforations of the sealing gasket facing each other and delimiting a plurality of independent sealed filter zones on said at least one filter;
   forced filtering means; and
   filtrate evacuation means;
   said upstream clamping block being made in the form of a removable independent tank block so that samples introduced in the wells thereof can be pretreated outside said strand, and said upstream and downstream clamping blocks being provided with complementary fixing means for securing the clamping blocks together;
   said stand having a front opening configured so as to enable the assembly formed by said upstream and downstream clamping blocks to be inserted therein, and having a top opening to enable said forced filtering means to be applied to the upstream clamping block.

2. A filter device according to claim 1, including removable closure means provided on the upstream face of the upstream clamping block, so that in the event that the samples need to be pretreated prior to filtering, the assembly can be turned over, the closure means removed and said assembly inserted in the stand.

3. A filter device according to claim 1, wherein said stand includes horizontal slideways for receiving the assembled upper and lower clamping blocks like a drawer.

4. A filter device according to claim 1, wherein said complementary fixing means for securing the clamping blocks together comprise complementary engaging studs.

5. A filter device according to claim 1, wherein the downstream face of the upstream clamping block and the upstream face of the downstream clamping block are provided with complementary indexing means ensuring that the perforations of the gasket are in alignment with the perforations of the upstream clamping block and of the at least one filter.

6. A filter device according to claim 1, wherein the forced filtering means comprise means for applying pressure to the samples contained int he wells of the clamping block, and are provided in a moving head including a pressurizing chamber whose floor has a first plurality of tubes passing therethrough, which tubes are calibrated and designed to be inserted in part into the wells of the upstream clamping block and communicating with an inlet for air under pressure provided through the ceiling of said chamber, the outside diameter of the calibrated tubes being substantially equal to the inside diameter of the wells, said chamber being movable under drive from an actuator.

7. A filter device according to claim 6, wherein the ceiling of the pressurizing chamber has a plurality of tubes passing therethrough and received inside the calibrated tubes in the floor of said chamber, the ceiling tubes being in communication with a device for feeding a substance for treating the particles retained by the independent filter zones after the samples have been filtered.

8. A filter device according to claim 6, wherein the fixing means for at least the upstream face of the clamping block comprises a discardable adhesive membrane and the calibrated tubes of the forced filtering means are chamfered, enabling said membrane to be left in place and then punctured locally by the chamfered tubes when the said forced filtering means are applied.

9. A filter device according to claim 1, wherein said filtrate evacuation means comprises a tank mounted in the lower part of said stand, the downstream clamping block being applied in sealed manner on said tank when said downstream block is inserted in said stand.

10. A filter device according to claim 9, wherein said tank is in communication with an opening provided through the bottom face of said stand.

11. A filter device according to claim 1, wherein the filter device includes two filters having different pore sizes placed on opposite sides of the perforated gasket, the filter having the smaller pore size being placed downstream so as to enable a double filtering.

12. A filter device according to claim 1, wherein the evacuation means is removable and comprises a block which is identical to the clamping block and which includes removable closure means for its downstream face, said evacuation means comprising a tank being intended, after the first filtering operation, to replace the upstream clamping block and to be replaced by normal evacuation means so as to enable a second filtering operation to be performed on a second at least one filter that replaces the first at least one filter.

13. A filter device according to claim 1, wherein said device includes a second upstream clamping block and a second downstream clamping block with a second perforated gasket and a second at least one filter being interposed therebetween, and being disposed in cascade relative to the first upstream clamping block and to the first downstream clamping block, the stand including two further horizontal slideways for enabling the second downstream clamping block to be inserted therein together with the second upstream clamping block it supports.

14. A filter device according to claim 1, wherein the downstream clamping block is designed to cooperate with a plurality of mutually identical upstream clamping blocks with the number of blocks being a function of the number of samples.

15. A filter device according to claim 1, wherein the forced filtering means further include filtrate suction means in communication with said filtrate evacuation means.

16. A filter device according to claim 1, wherein said device is automatic and programmable and the forced filtering means are themselves also programmable, the device being under the control of a controlling computer.

* * * * *